(12) United States Patent
Froberg

(10) Patent No.: US 6,264,498 B1
(45) Date of Patent: Jul. 24, 2001

(54) FEMALE CONNECTOR PART FOR A PACER HOUSING

(75) Inventor: Paul Froberg, Bromma (SE)

(73) Assignee: Pacesetter AB, Järfälla (SE)

( * ) Notice: Subject to any disclaimer, the term of this patent is extended or adjusted under 35 U.S.C. 154(b) by 0 days.

(21) Appl. No.: 09/581,409

(22) PCT Filed: Dec. 1, 1998

(86) PCT No.: PCT/SE98/02194

§ 371 Date: Jun. 12, 2000

§ 102(e) Date: Jun. 12, 2000

(87) PCT Pub. No.: WO99/30778

PCT Pub. Date: Jun. 24, 1999

(30) Foreign Application Priority Data

Dec. 12, 1997 (SE) .................................................. 9704645

(51) Int. Cl.[7] .................................................. H01R 4/24
(52) U.S. Cl. .......................................................... 439/441
(58) Field of Search .................................. 439/441, 267, 439/629, 436–440

(56) References Cited

U.S. PATENT DOCUMENTS 3,336,916 * 8/1967 Edlich .................................. 439/267
4,428,635 * 1/1984 Hamsler, Jr. et al. ................ 439/267
5,252,090   10/1993 Giurtino et al. .
5,320,558    6/1994 von Roretz .
6,012,944 * 1/2000 Hatakeyama ......................... 439/441

* cited by examiner

Primary Examiner—Brian Sircus
Assistant Examiner—J. F. Duverne
(74) Attorney, Agent, or Firm—Schiff Hardin & Waite

(57) ABSTRACT

The above objects are achieved in accordance with the principles of the present invention in a female connector part for cooperation with an elongated male connector part, the female connector part being intended for use in a pacemaker housing and having a longitudinal bore adapted to receive the male connector part. An element carrying resilient tongues, disposed at a small inward angle, i.e. inward from the opening of the female connector part, relative to a plane orthogonal to the longitudinal axis of the bore. The tongues are movable between a first position at which the respective tips of the tongues can engage the male connector part in the bore, and a second position at which the tips of the tongues do not engage the male connector part in the bore. The female connector part also includes a sleeve which is movable between two positions respectively corresponding to the first and second positions of the tongues. In a first position of the sleeve, the tongues are free to engage the male connector part in the bore, and in a second position of the sleeve, the sleeve is located between the tongues and the male connector part, thereby precluding the tongues from engaging the male connector part.

5 Claims, 3 Drawing Sheets

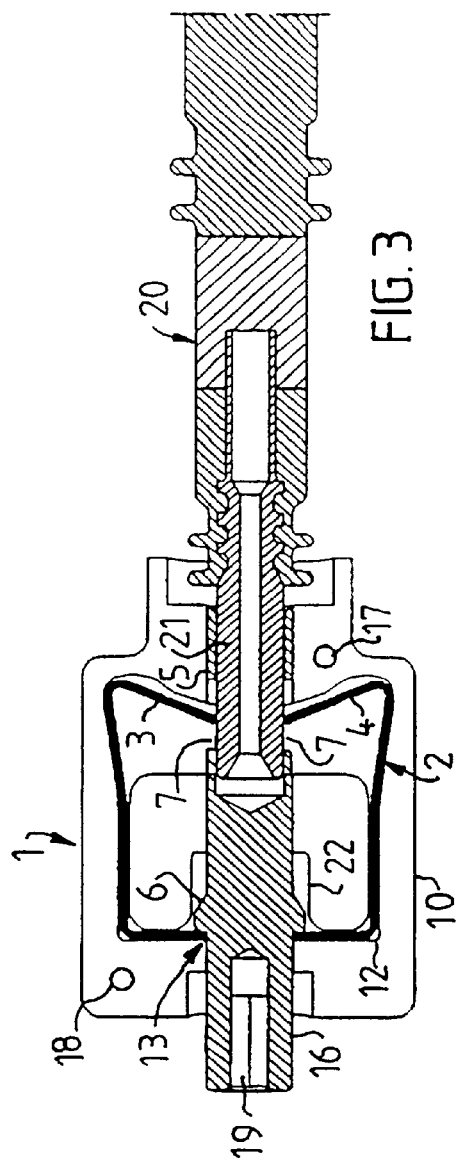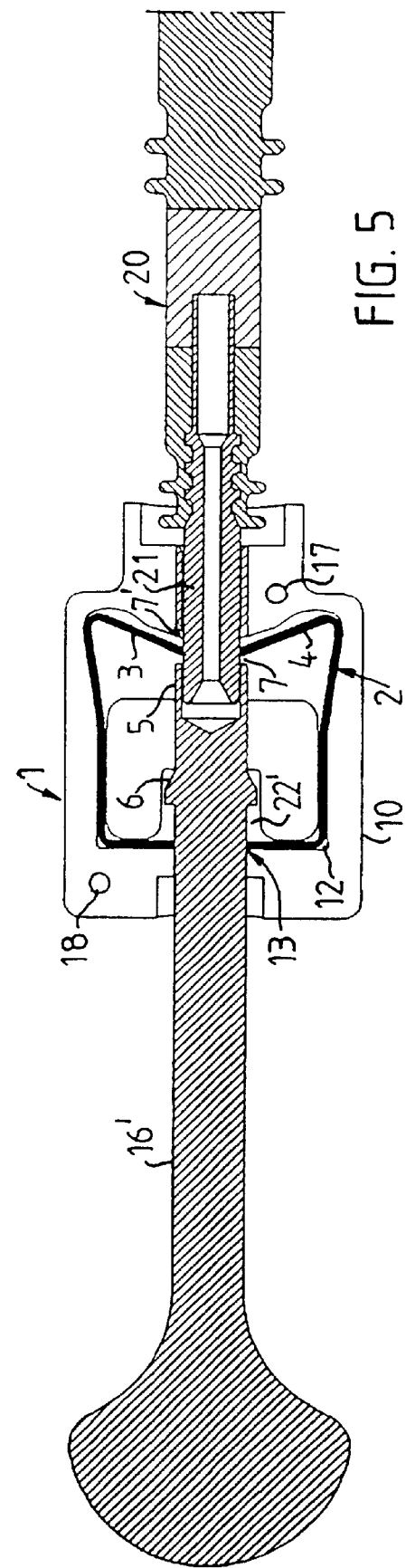

FEMALE CONNECTOR PART FOR A PACER HOUSING

FIELD OF THE INVENTION

The present invention relates to a connector of a type suitable for connecting a lead to a housing of an implantable pacer.

BACKGROUND OF THE INVENTION

A pacer system normally includes a pulse generator located in a pacer housing, one or more leads and each having an electrode at the distal end thereof. The proximal end of each lead is connected to the pacer housing by means of a releasable connector. The connector includes a female connector part in the pacer housing. The proximal end of the lead normally is designed as a standardized male connector part and the female connector part normally is standardized to such an extent that it will receive this standardized male connector part. The most common way of fixing or locking the male connector part in the female connector part is to use set screws, which are oriented in an orthogonal direction in relation to the male connector part and which are accessible from the outside of the pacer housing. The female connector part normally is located in a header molded on to the housing.

Although these set screws generally have a good fixing effect, the screws are somewhat difficult to handle, the screws being small and easily lost, both during transport and storage and during implantation. For this reason, attempts have been made to develop fixing means, which more or less automatically lock the male connector part upon insertion thereof.

One device in which the proximal end of the lead is locked automatically is disclosed in U.S. Pat. No. 5,252,090. This device includes two elastically resilient metal tongues in a female connector part. The tongues are situated in a common plane and have a common central line, with a respective free end, which are located oppositely to each other. The distance between the two free ends is smaller than the diameter of the male connector part. The tongues will be deflected into the direction of insertion when the male connector part is inserted into the female connector part and the tongues thus will engage and lock the sides of the male connector part. If the male connector part is pulled outwardly from the female connector part, the locking effect will increase. This is because the friction between the tongues and the male connector part will draw the tongues in closer contact with the male connector part. The two tongues are integrally connected to two wings extending through openings in a header molded onto the housing. The wings are angled in relation to the plane of the tongues. Pressure on the wings will move the tongues out of engagement with the male connector part, which then can be removed.

In similarity with the design using set screws, the locking means in the above design have to be accessed laterally from the outside. For this reason, the locking means are located in the header in order to avoid openings for manipulation in the parts of the housing in which the electronic parts of the pacer are located. Any openings for the connections in the housing or can into the interior of the housing from the header thus can be permanently sealed.

SUMMARY OF THE INVENTION

And object of the invention is to provide a connection of the kind described above, which can use standard male connector parts, which involves a positive locking effect and which does not need any lateral openings in the connector housing or the pacemaker housing. Lateral openings are relatively difficult to design and manufacture, particularly if the connection is placed in the pacemaker housing. At the same time, it should be possible to easily remove the male connector part without any need of manual operations. A further object is to provide a connector that is suitable for use in so called black holes. Black holes are connectors made directly in the pacer housing without any need for the commonly used molded-on connector parts in the form of headers. The black holes may or may not extend through the entire pacer housing. A black hole extending through the entire housing gives the possibility to access the release mechanism from the outside without any need of lateral openings, the mechanism in this case being accessible longitudinally from the end of the hole.

The above objects are achieved in accordance with the principles of the present invention in a female connector part for cooperation with an elongated male connector part, the female connector part being intended for use in a pacemaker housing and having a longitudinal bore adapted to receive the male connector part. An element carrying resilient tongues, disposed at a small inward angle, i.e. inward from the opening of the female connector part, relative to a plane orthogonal to the longitudinal axis of the bore. The tongues are movable between a first position at which the respective tips of the tongues can engage the male connector part in the bore, and a second position at which the tips of the tongues do not engage the male connector part in the bore. The female connector part also includes a sleeve which is movable between two positions respectively corresponding to the first and second positions of the tongues. In a first position of the sleeve, the tongues are free to engage the male connector part in the bore, and in a second position of the sleeve, the sleeve is located between the tongues and the male connector part, thereby precluding the tongues from engaging the male connector part.

SHORT DESCRIPTION OF THE APPENDED DRAWINGS

FIG. 3 shows a longitudinal section of the components of the female connector part of FIG. 1 in an assembled state.

FIG. 5 shows a longitudinal section of the components of the female connector part of FIG. 4 in an assembled state.

DESCRIPTION OF THE PREFERRED EMBODIMENT

Figure 1:
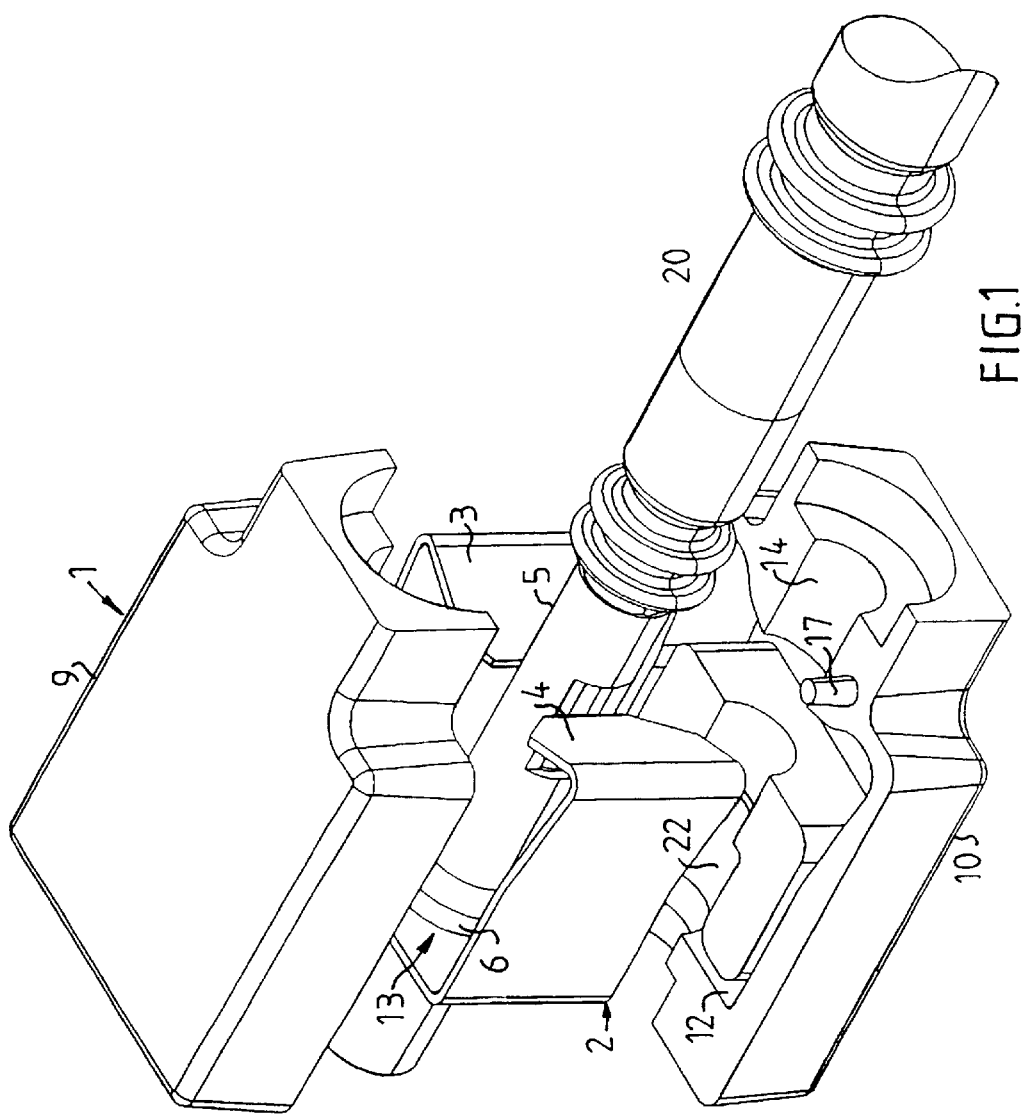
FIG. 1 illustrates a first embodiment of a female connector part in accordance with the invention in a perspective, exploded view.

A first embodiment of the invention is described in FIG. 1.

The female connector part has a housing 1 formed by two halves 9,10 that are mirror symmetric. The two halves 9,10 in the assembled state define a central bore 14 and a U-shaped groove 12 whose base is orthogonal to the central opening. The two halves 9,10 also each have a pin 17 and a complementary guide hole 18 for guiding the two parts when they are assembled.

The groove 12 is intended to hold a U-shaped spring 2. The base of the spring 2 is provided with an opening 13 corresponding to the central bore 14. The opening 13 is aligned with the central opening 14 when the halves 9,10 of the housing 1 and the spring 2 has been assembled.

The female connector part 1 is intended to receive the contact pin 21 of a standard male connector part 20 of a standard lead for a pacer. For the purposes of this description, the part of the female connector through which the male connector part is to be inserted will be defined as the proximal end. The opposite end will be defined as the distal end.

The central bore 14 houses a release part 16 comprising a proximal cylindrical sleeve 5. The central bore 8 of the sleeve 5 has a diameter that corresponds to the diameter of the contact pin 21. The sleeve 5, which extends through the opening 13 in the spring 2, is provided with a flange 6 engaging the proximal side of the base of the spring 2. The central bore 14 is provided with a corresponding recess 22 for the flange 6. The distal end of the release part 16 is provided with operating means in the shape of a longitudinal hex socket 19. By means of this socket, the sleeve 5 can be rotated with a suitable tool. The socket 19 is accessible from the outside of the pacer, and the female connector part thus is very suitable for a black hole open at both ends. The female connector part of course also can be molded into a header that is provided with two openings.

The sleeve 5 further is provided with two lateral openings 7,7' located opposite to each other. The longitudinal edges of the openings 7,7' are beveled.

The free ends of the shanks of the U-shaped spring 2 are bent inwardly to such an extent that they are oriented a small angle toward the distal end of the connector part 1. This angle refers to a plane that is orthogonal to the longitudinal direction of the bore 14. In this way, the free ends form locking tongues 3,4. The locking tongues 3,4 are free to be deflected, but the outside of the remaining parts of the shanks of the spring are blocked against outward movement by the walls of the housing 1. The tongues 3,4 are located the same distance from the proximal end of the sleeve 5 as the center of the openings 7,7' in the sleeve 5. The tongues 3,4 thus can engage a contact pin 21 inserted into the sleeve 5 when the openings 7,7' are aligned with the tongues 3,4.

Normally the openings 7,7' are aligned with the tongues 3,4. Thus, when the contact pin 21 is inserted into the sleeve 5, the tongues, which protrude through the openings 3,4, will lock the contact pin 21 against removal in the same manner as in the above-identified U.S. Pat. No. 5,252,090. No tool is thus needed for locking the male connector part in the female connector part.

When the contact pin 21 and lead is to be disconnected from the female connector part, an Allen key is inserted into the hex socket 19 and the sleeve 5 is turned 90°. The tips of the tongues 3,4 then will slide up on the outside of the sleeve, thus being held out of engagement with the contact pin 21. The contact pin then easily can be removed from the sleeve and from the female connecting part.

Figure 2:
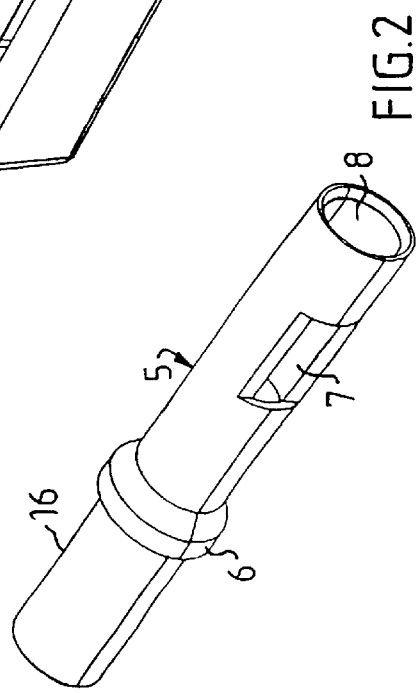
FIG. 2 shows a sleeve according to the invention as used in the embodiment according to FIG. 1.
Figure 4:
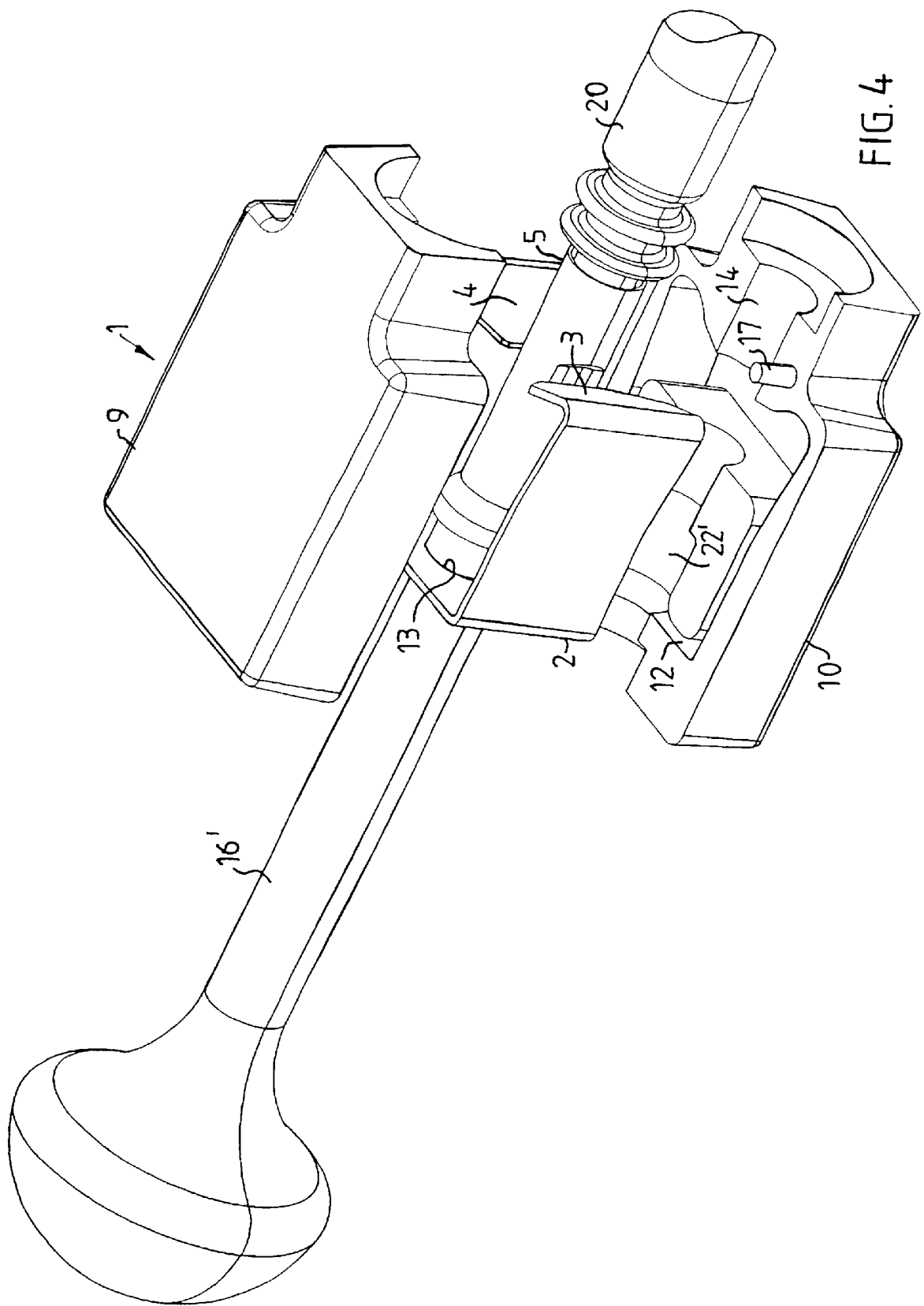
FIG. 4 illustrates a second embodiment of a female connector part in accordance with the invention in a perspective, exploded view.

FIGS. 4 and 5 illustrate another embodiment of the invention. This embodiment is identical to the one described above except that the part of the sleeve 5 containing the hex socket has been modified. The elements in FIGS. 4 and 5 that are identical to elements in FIGS. 1–3 thus have been given the same reference signs as those elements have.

The embodiment according to FIGS. 4 and 5 thus has a housing 1 formed by two halves 9,10 and defining a central bore 14 and a U-shaped groove 12. The housing 1 further has a U-shaped spring 2 located in the groove 12. The spring 12 is provided with an opening 13 in the base of the U and the free ends of the shanks of the U are bent inwardly. The central bore 14 houses a release element 16' having the sleeve 5 with lateral openings 7,7' and a flange 6.

The operating element in this embodiment is a rod-shaped extension 16' of the sleeve 5. The rod 16' is permanently attached to the sleeve 5 and the rod 16' extends out of the housing of the pacer.

The contact pin 21 is locked in the female connection part by inserting the pin 21 into the sleeve 5.

There are two possibilities when designing the release operation in this case.

The first possibility is to rotate the rod 16', as in the first embodiment described above. In that case, the longitudinal edges of the openings 7,7' should be beveled as described above.

The second possibility, which is illustrated in FIGS. 4 and 5, is to design the release means for longitudinal movement, particularly for a movement in which the rod 16' is pulled out of the pacer housing. In this case, the proximal edges of the lateral openings 7,7' in the sleeve 5 should be beveled so that the tips of the tongues 3,4 can slide up onto the proximal part of the sleeve 5. When the rod 16' is pulled out of the pacer, the contact pin consequently will be released. It should be noted that in this case the recess 22' should have a length that is sufficient to allow this longitudinal movement.

Although the lateral openings in the sleeve 5 have been illustrated as being roughly rectangular, other shapes are possible. The openings can for instance be circular or may extend to the end of the sleeve 5.

Although modifications and changes may be suggested by those skilled in the art, it is the intention of the inventor to embody within the patent warranted hereon all changes and modifications as reasonably and properly come within the scope of his contribution to the art.

What is claimed is:

1. A female connector part for cooperation with an elongate, male connector part, said female connector part being adapted for use in a pacer housing, said female connector part comprising a longitudinal bore having an opening and a longitudinal axis and defining a longitudinal space for said male connector part, said space comprising resilient tongues, forming an inward angle proceeding away from said opening and being measured relative to a plane that is orthogonal to said longitudinal axis, said tongues being movable between a first position in which tips of the tongues are adapted to engage said male elongate connector part when in said bore and a second position in which the tips of the tongues are adapted not to engage the male elongate connector part when in said bore, and a sleeve movable between two positions respectively corresponding to said first and second positions of said tongues comprising a first sleeve position, in which said tongues are free to engage said male connector part when in said bore, and a second sleeve position in which said sleeve is adapted to be located in-between said tongues and said male connector part when in said bore, said tongues being forced by said sleeve out of engagement with said male connector part.

2. A female connector part according to claim 1 wherein said sleeve comprises at least one traverse beveled edge for each of said tongues which is movable in a direction of said longitudinal axis from a first edge position, which is distal to the opening and in which said tongues are adapted to be in engagement with aid male connector part when in said bore, to a proximal position in which said tongues are supported by said sleeve.

3. A female connector part according to claim 1, wherein said sleeve is rotatable around the longitudinal axis between said first and second sleeve positions, and comprises at least one longitudinal beveled edge for each of said tongues so that said tongues are adapted to engage said male connector part when in said bore in said first sleeve position of said sleeve and said tongues are supported by said sleeve in said second sleeve position.

4. A female connector part according to claim 3, wherein said sleeve is cylindrical and surrounds said male connector part wherein said bore, said sleeve having a wall with at least one part of the wall being cut away for each of said tongues, the edges of said cut away parts forming the respective beveled edges.

5. A female connector part according to claim 2, wherein said sleeve is cylindrical and surrounds said male connector part wherein said bore, said sleeve having a wall with at least one part of the wall being cut away for each of said tongues, the edges of said cut away parts forming the respective beveled edges.

* * * * *